United States Patent [19]
Wettenhall et al.

[11] Patent Number: 6,054,163
[45] Date of Patent: Apr. 25, 2000

[54] *BACTERIOCIN PISCICOLIN* 126

[75] Inventors: Richard Edward Hugh Wettenhall, Camberwell; Barrie Ernest Davidson, North Melbourne; Alan James Hillier, Ferntree Gully; Kim Harmark, Carlton, all of Australia; Ralph Wilson Jack, Bonn-Venusberg, Germany; Malcolm Wayne Hickey, Geelong, Australia; John Coventry, Strathmore, Australia; Jason Wan, Hoppers Crossing, Australia

[73] Assignees: The University of Melbourne, Victoria; Commonwealth Scientific and Industrial Research Organisation, Act; Daratech Pty Limited, Victoria, all of Australia

[21] Appl. No.: 08/894,483

[22] PCT Filed: Feb. 22, 1996

[86] PCT No.: PCT/AU96/00096

§ 371 Date: Jun. 26, 1998

§ 102(e) Date: Jun. 26, 1998

[87] PCT Pub. No.: WO96/26216

PCT Pub. Date: Aug. 29, 1996

[30] Foreign Application Priority Data

Feb. 22, 1995 [AU] Australia ................................. PN1310

[51] Int. Cl.$^7$ ................................................... A61K 38/16
[52] U.S. Cl. .............................. 426/335; 426/36; 530/324
[58] Field of Search ............................... 426/36, 335, 654, 426/582; 530/324

[56] References Cited

FOREIGN PATENT DOCUMENTS

WO 95/06663   3/1995   WIPO .

OTHER PUBLICATIONS

Worobo et al, "Characteristics and genetic determinant of a . . . ," Microbiology, vol. 140, pp. 517–526 (1994).

Jack et al, "Characterization of the Chemical and Antimicrobial Properties," Applied and Environmental Microbiology, vol. 62, No. 8, pp. 2897–2903 (1996).

Fems Microbiology Letters, vol. 115, 1994, A. Holck et al., Purification and Cloning of Sakacin 674, a Bacteriocin from *Lactobacillus sake* Lb 674 pp. 143–149.

Journal of General Microbiology, vol. 138, 1992, A. Holck et al., Purification and Amino Acid Sequence of Sakacin A, a Bacteriocin from *Lactobacillus sake* Lb 706, pp. 2715–2720.

The Journal of Biological Chemistry, vol. 269, No. 16, 1994, L. Quadri et al., Chemical and Genetic Characterization of Bacteriocins Produced by *Carnobacterium piscicola* LV17B, pp. 12204–12211.

Applied and Environmental Microbiology, vol. 58, No. 8, 1992, J. Marugg et al., Cloning Expression and Nucleotide Sequence of Genes Involved in Production of Pediocin PA–1, a Bacteriocin from *Pediococcus acidilactici* PAC 1.0,, pp. 2350–2367.

Microbiology, vol. 140, 1994, P. Tichaczek et al., Cloning and Sequencing of Sak P Encoding Sakacin P, the Bacteriocin Produced by *Lactobacillus sake* LTH 673, pp. 2360–2367.

Waite Library, Department of Food Science, University of Alberta, Edmonton, Alberta, Canada, T6G 2P5, Chapter 18, "Bacteriocins Produced by Carnobacterium Species", Michael E. Stiles, pp. 451–459, 1996.

Applied and Environmental Microbiology, Aug. 1990, p. 2503–2510, vol. 56, No. 8, "Plasmid–Associated Bacteriocin Production by a Strain of *Carnobacterium piscicola* from meat".

*Primary Examiner*—Keith D. Hendricks
*Attorney, Agent, or Firm*—Nixon & Vanderhye

[57] ABSTRACT

The present invention provides a bacteriocin having a molecular weight of about 4.4 kDa and methods involving the use of this bacteriocin. The bacteriocin preferably has an amino acid sequence as shown in SEQ ID NO:5 (FIG. 3). The present invention also provides a DNA molecule encoding this bacteriocin.

3 Claims, 6 Drawing Sheets

1                                                                          15
Lys-Tyr-Tyr-Gly-Asn-Gly-Val-Ser-Cys-Asn-Lys-Asn-Gly-Cys-Thr-
16                                                                         30
Val-Asp-Trp-Ser-Lys-Ala-Ile-Gly-Ile-Ile-Gly-Asn-Asn-Ala-Ala-
31                                                      44
Ala-Asn-Leu-Thr-Thr-Gly-Gly-Ala-Ala-Gly-Trp-Asn-Lys-Gly

```
  1 CGATGTTACA ATCAATTAAC TTTATAAGTT CATGAATAAT ATCGTGATAG
 51 TTCAGGAATA AAAAATCTAT AAGTAAAAAA GATGTGATAC AGTCAGCATG
101 TTGTAAAAAA TATTTTAAAA AGGAGCGTGT TTACGCATGA AAACTGTTAA
151 AGAACTTAGC GTTAAAGAAA TGCAACTAAC TACAGGAGGT AAGTATTACG
201 GAAATGGCGT TTCCTGTAAT AAAAATGGTT GTACTGTAGA TTGGAGCAAA
251 GCTATTGGGA TTATAGGAAA CAATGCAGCA GCAAATTTGA CTACAGGTGG
301 AGCCGCTGGT TGGAACAAAG GATAATTAAA GTCTCTTATT TTTTATCTTG
351 TAAAAAAGAT GATACGCATC AATGCTGTGA CATAACATAG ATGGGTCTTT
401 ATATTTGTAA GTTACATTTA AAACAAAAAT AAATATATAA AAATATTTTT
451 TTATAGTCTT AGGAATTATG TTATACTAAC AAAAATAGGC TAGTTTCAAC
501 ATGATGTAAA GAAACTTATA CTATCAACTA AATCATAAA TATATAAAT
551 TAAGGAGTGA TATTTTATGG GTAAGTTAAA ATGGTTTCT GGAGGAAAAG
601 AACGATC
```

Fig.5

```
MetLysThrValLysGluLeuSerValLysGluMetGlnLeuThr
ATGAAAACTGTTAAAGAACTTAGCGTTAAAGAAATGCAACTAACT    45

ThrGlyGlyLysTyrTyrGlyAsnGlyValSerCysAsnLysAsn
ACAGGAGGTAAGTATTACGGAAATGGCGTTTCCTGTAATAAAAAT    90

GlyCysThrValAspTrpSerLysAlaIleGlyIleIleGlyAsn
GGTTGTACTGTAGATTGGAGCAAAGCTATTGGGATTATAGGAAAC   135

AsnAlaAlaAlaAsnLeuThrThrGlyGlyAlaAlaGlyTrpAsn
AATGCAGCAGCAAATTTGACTACAGGTGGAGCCGCTGGTTGGAAC   180

LysGly***
AAAGGATAA         189
```

Fig.6

```
                        SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Primer"

(iii) HYPOTHETICAL: NO (iv) ANTI-SENSE: NO (xi) SEQUENCE DESCRIPTION: SEQ ID NO: 1:

GAGTTTGATC CTGGCTCAG                                                  19

(2) INFORMATION FOR SEQ ID NO: 2:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Primer"

(iii) HYPOTHETICAL: NO (iv) ANTI-SENSE: NO (xi) SEQUENCE DESCRIPTION: SEQ ID NO: 2:

TACAAGGCCC GGGAACG                                                    17

(2) INFORMATION FOR SEQ ID NO: 3:

(i) SEQUENCE CHARACTERISTICS:
        (A) LENGTH: 26 base pairs
        (B) TYPE: nucleic acid
```

(C) STRANDEDNESS: single
        (D) TOPOLOGY: linear (ii) MOLECULE TYPE: other nucleic acid
        (A) DESCRIPTION:   /desc = "Primer"

(iii) HYPOTHETICAL: NO (iv) ANTI-SENSE: NO (xi) SEQUENCE DESCRIPTION: SEQ ID NO: 3:

TGCTAACTAA AGAACTGGAC GTTGCT                                                   26

(2) INFORMATION FOR SEQ ID NO: 4:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Primer"

(iii) HYPOTHETICAL: NO (iv) ANTI-SENSE: NO (xi) SEQUENCE DESCRIPTION: SEQ ID NO: 4:

GCCTTTAGTT CCAACGTCCA CGTGCACGTG CACGTCC                                       37

(2) INFORMATION FOR SEQ ID NO: 5:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Carnobacterium piscicola
        (B) STRAIN: JG126

(xi) SEQUENCE DESCRIPTION: SEQ ID NO: 5:

Lys Tyr Tyr Gly Asn Gly Val Ser Cys Asn Lys Asn Gly Cys Thr Val
1               5                   10                  15

Asp Trp Ser Lys Ala Ile Gly Ile Ile Gly Asn Asn Ala Ala Ala Asn
            20                  25                  30

Leu Thr Thr Gly Gly Ala Ala Gly Trp Asn Lys Gly
        35                  40

(2) INFORMATION FOR SEQ ID NO: 6:

(i) SEQUENCE CHARACTERISTICS:
        (A) LENGTH: 607 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Carnobacterium piscicola
            (B) STRAIN: JG126

(xi) SEQUENCE DESCRIPTION: SEQ ID NO: 6:

CGATGTTACA ATCAATTAAC TTTATAAGTT CATGAATAAT ATCGTGATAG TTCAGGAATA     60

AAAAATCTAT AAGTAAAAAA GATGTGATAC AGTCAGCATG TTGTAAAAAA TATTTTAAAA    120

AGGAGCGTGT TTACGCATGA AAACTGTTAA AGAACTTAGC GTTAAAGAAA TGCAACTAAC    180

TACAGGAGGT AAGTATTACG GAAATGGCGT TTCCTGTAAT AAAAATGGTT GTACTGTAGA    240

TTGGAGCAAA GCTATTGGGA TTATAGGAAA CAATGCAGCA GCAAATTTGA CTACAGGTGG    300

AGCCGCTGGT TGGAACAAAG GATAATTAAA GTCTCTTATT TTTTATCTTG TAAAAAAGAT    360

GATACGCATC AATGCTGTGA CATAACATAG ATGGGTCTTT ATATTTGTAA GTTACATTTA    420

AAACAAAAAT AAATATATAA AAATATTTTT TTATAGTCTT AGGAATTATG TTATACTAAC    480

AAAAATAGGC TAGTTTCAAC ATGATGTAAA GAAACTTATA CTATCAACTA AAATCATAAA    540

TATATAAAAT TAAGGAGTGA TATTTTATGG GTAAGTTAAA ATGGTTTTCT GGAGGAAAAG    600

AACGATC                                                             607

(2) INFORMATION FOR SEQ ID NO: 7:

(i) SEQUENCE CHARACTERISTICS:
            (A) LENGTH: 189 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Carnobacterium piscicola
            (B) STRAIN: JG126

(xi) SEQUENCE DESCRIPTION: SEQ ID NO: 7:

ATGAAAACTG TTAAAGAACT TAGCGTTAAA GAAATGCAAC TAACTACAGG AGGTAAGTAT     60

TACGGAAATG GCGTTTCCTG TAATAAAAAT GGTTGTACTG TAGATTGGAG CAAAGCTATT    120

GGGATTATAG GAAACAATGC AGCAGCAAAT TTGACTACAG GTGGAGCCGC TGGTTGGAAC    180

AAAGGATAA                                                            189

(2) INFORMATION FOR SEQ ID NO: 8:

(i) SEQUENCE CHARACTERISTICS:
            (A) LENGTH: 62 amino acids
            (B) TYPE: amino acid
            (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
            (A) ORGANISM: Carnobacterium piscicola
            (B) STRAIN: JG126

(xi) SEQUENCE DESCRIPTION: SEQ ID NO: 8:

```
Met Lys Thr Val Lys Glu Leu Ser Val Lys Glu Met Gln Leu Thr Thr
1               5                   10                  15

Gly Gly Lys Tyr Tyr Gly Asn Gly Val Ser Cys Asn Lys Asn Gly Cys
                20                  25                  30

Thr Val Asp Trp Ser Lys Ala Ile Gly Ile Ile Gly Asn Asn Ala Ala
            35                  40                  45

Ala Asn Leu Thr Thr Gly Gly Ala Ala Gly Trp Asn Lys Gly
    50                  55                  60
```

BACTERIOCIN PISCICOLIN 126

This invention relates to novel bacteriocin molecules having antimicrobial activity. In one particular application, the bacteriocin according to the invention is used as a food preservative.

BACKGROUND OF THE INVENTION

There is a continual need for new food preservatives bearing new and useful properties. Further, there is growing interest in replacing traditional "chemical" food preservatives with effective "natural" preservatives, especially those which are specific for pathogenic microorganisms and do not harm beneficial food-producing strains. In this regard, considerable research has been conducted on bacterial peptides known as bacteriocins which are often heat stable and have antimicrobial activity. Two such bacteriocins which are commercially produced for use as food preservatives are nisin and pediocin PA-1. Nisin has been given the status of Generally Regarded as Safe for human consumption (GRAS) by the United States FDA. Nisin and pediocin PA-1 however, have broad spectrum activity, affecting not only pathogenic, but also beneficial (in the food system) microorganisms.

SUMMARY OF THE INVENTION

Novel bacteriocins having a range of activity that is different to and preferably narrower than those of nisin and pediocin PA-1 would be desirable. The present inventors have now identified and isolated a new bacteriocin which has a limited range of activity in comparison to, for example, nisin and pediocin PA-1.

Thus, in a first aspect, the present invention consists in a substantially pure preparation of a bacteriocin having a molecular mass of about 4.4 kDa and antimicrobial activity substantially according to Table 2.

Figure 3:
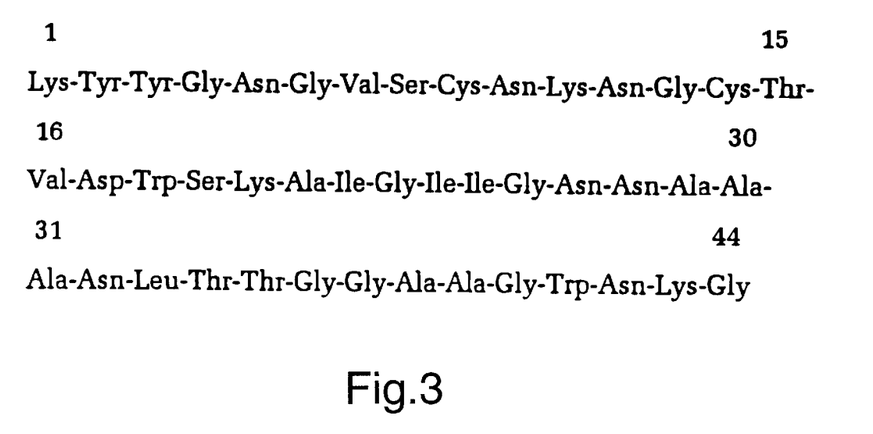
FIG. 3. Amino Acid Sequence of Piscicolin 126.

In a preferred embodiment of the present invention the bacteriocin has an amino acid sequence substantially identical to the sequence shown in FIG. 3.

In a second aspect the present invention consists in a biologically pure culture of bacterial strain JG126.

A sample of bacterial strain JG126 was deposited under the Budapest Treaty with Australian Government Analytical Laboratories (AGAL), 1 Saukin Street, Pymble, New South Wales, Australia, on Dec. 21 1994, and was accorded accession No. N94/61478.

In a third aspect the present invention consists in an isolated DNA molecule encoding the bacteriocin of the first aspect of the present invention.

Figure 6:
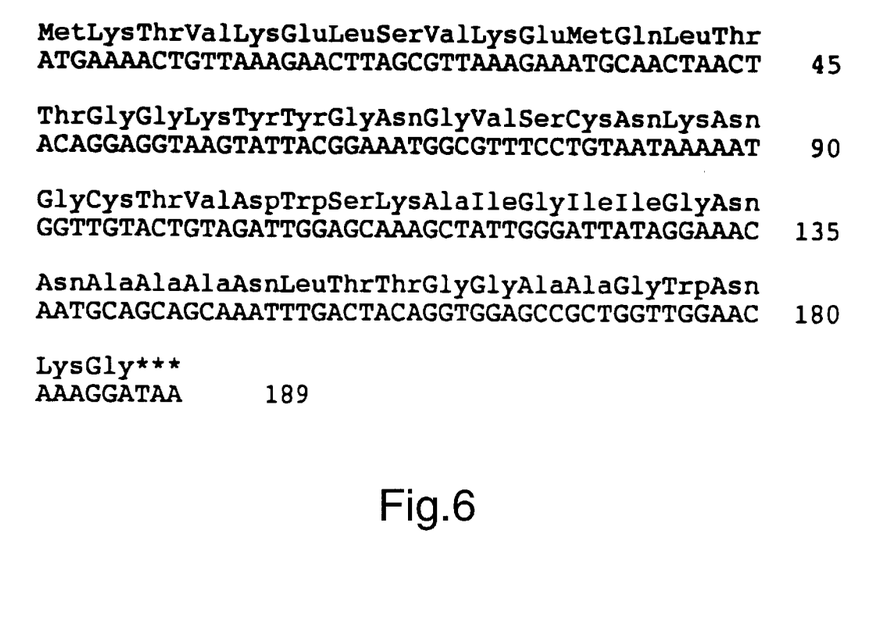
FIG. 6. DNA sequence and translation of gene encoding Piscicolin 126 and its putative signal peptide.

In a preferred embodiment of this aspect of the present invention the DNA molecule includes a nucleotide sequence as shown in FIG. 6.

In a fourth aspect the invention consists in a method of preserving foods or beverages, the method comprising adding to the food or beverage an effective antimicrobial amount of a bacteriocin of the first aspect of the present invention.

The bacteriocin of the present invention may be isolated from natural sources, or produced by recombinant DNA techniques well known in the art.

BRIEF DESCRIPTION OF THE DRAWINGS

In order that the nature of the present invention may be more clearly understood, preferred forms thereof will now be described with reference to the following non-limiting examples and the accompanying figures.

Figure Legends

A sample of purified piscicolin 126 was co-analysed along with the bacteriocin SA-FF22 (m=2794.3) and porcine insulin (m=5777.6) and the instrument was calibrated accordingly. From 36 mass spectra recorded, a mass estimate of m=4416.6 ±1.9 was calculated for piscicolin 126.

FIGS. 4A–C: Analysis of the products formed following treatment of piscicolin 126 with the alkylating agent 4-vinylpyridine in either the presence or absence of a reducing agent.

FIG. 4C: D peak material from B. No mass increase was observed in A (sample without reducing agent) suggesting that piscicolin 126 does not contain free sulphydryl groups while the mass increase in D (210 Da) corresponds to bi-pyridethylation and suggests the piscicolin 126 contains a disulphide bridge between the two cysteine residues.

EXAMPLES

The invention will now be described in more detail with reference to the following examples.

Example 1

Isolation and Characterisation of Bacteriocin-Producing Strain JG126

A number of Gram-positive bacteria were collected from a wide range of sources and assessed for antimicrobial activity. One strain, JG126, was isolated from ham and found to be a catalase negative, Gram-positive rod.

To establish the identity of this organism, 16S rDNA was amplified by the polymerase chain reaction (PCR) from chromosomal DNA of the producing organism using the primers 5'GAGTTTGATCCTGGCTCAG and 5'TACAAGGCCCGGGAACG, corresponding to nucleotides 9–27 and 1394–1378, respectively, in the *Eschericia coli* 16S rRNA numbering system. A partial nucleotide sequence of the PCR product was determined using primer 9–27 and the sequence compared to all 16S rRNA sequences in the ribosomal database of Australian National Genomic Information Service (ANGIS) using the program FastA. The nucleotide sequence was 100% identical to *Carnobacterium piscicola*, accession no. M58812 in GenBank and it was concluded that JG126 was a strain of *C. piscicola*.

A sample of this bacterium was deposited under the Budapest Treaty with Australian Government Analytical Laboratories (AGAL), 1 Saukin Street, Pymble, New South Wales, Australia, on Dec. 21, 1994, and was accorded accession No. N94/61478.

The activity of the bacteriocin (designated herein as piscicolin 126) was determined as follows by bioassay with *Listeria monocytogenes* 4A. Bacteriocin was serially diluted with sterile distilled water and aliquots of each dilution were applied to an MRS (de Man, Rogasa and Sharpe medium) agar plate and overlaid with 7 ml TSBYE (Tryptohe Soy broth supplemented with 0.6% (w/v) yeast extract) soft agar (0.6% (w/v)) seeded with $10^6$ cfu ml$^{-1}$ of *Listeria monocytogenes* 4A and incubated at 30° C. for 16 h. The activity of piscicolin 126 was expressed in Arbitrary Units (AU), defined as the reciprocal of the titre of the highest dilution demonstrating a detectable zone of growth inhibition in the indicator lawn culture.

Example 2

Purification of Piscicolin 126

Piscicolin 126 was purified in the following manner:

Overnight cultures of bacterial strain JG126 in acetate-free MRS grown at 22° C. were clarified by centrifugation.

The peptide was precipitated from the culture supernatant by the addition of ammonium sulphate to 80% saturation and the precipitate was recovered by centrifugation.

Figure 1A:
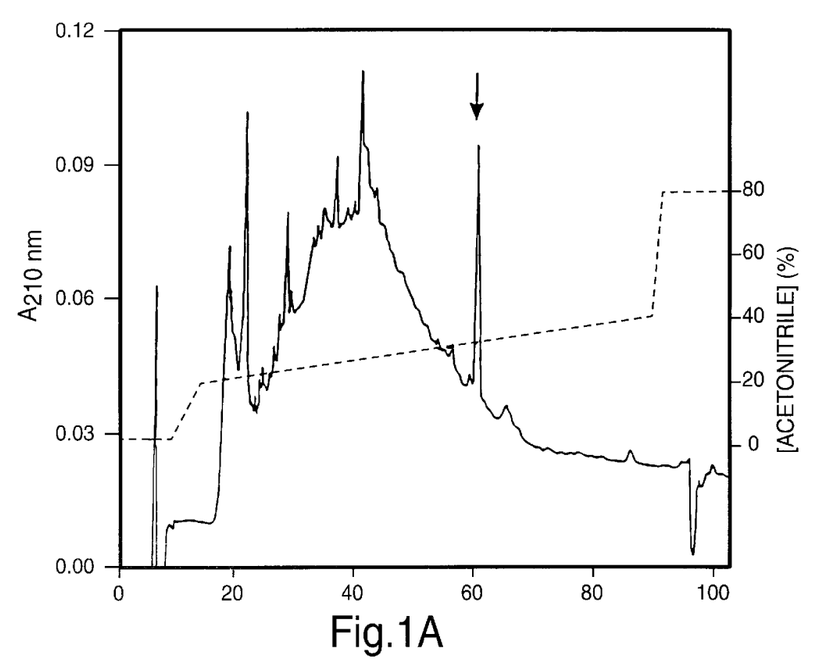
FIGS. 1A–1C: Purification of piscicolin 126 by reversed-phase HPLC (A) C18 reversed-phase HPLC separation of piscicolin 126 on a 4.6×250 mm Spherisorb ODS II (80 Å pore size, 5 μm particle size) column developed with the gradient of increasing acetonitrile concentration indicated by the dashed line. The piscicolin 126 had been previously partially purified by ion-exchange chromatography (not shown). The peak indicated by the arrow was collected and shown to have antimicrobial activity. (B) Rechromatography by C18 reversed-phase HPLC of the peak of piscicolin 126 collected as described in panel A. The column (2.1×250 mm Spherisorb ODS II [80 Å pore size, 5 μm particle size]) was developed with the gradient of increasing acetonitrile concentration indicated by the dashed line. (C) Electropherogram of purified piscicolin 126 separated by CZE through a 50 μm×50 cm uncoated silica capillary in 20 mM sodium citrate (pH 2.5) at 20 kV.
Figure 1B:
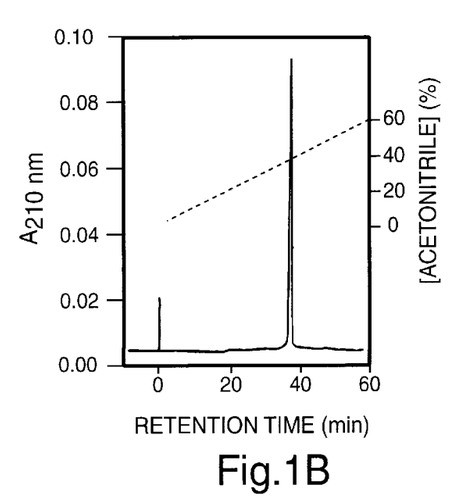

Peptide was purified by chromatography:

1. by ion exchange chromatography on CM-Sepharose Fast Flow; then
2. by semi analytical Reversed-phase HPLC on Spherisorb ODSII 4.6 ×250 mm, 80 Å, 5 mm particle (FIG. 1A); then
3. by analytical reversed-phase HPLC on Spherisorb ODSII 2.1×250 mm, 80 Å, 5 mm particle (FIG. 1B).

Figure 1C:
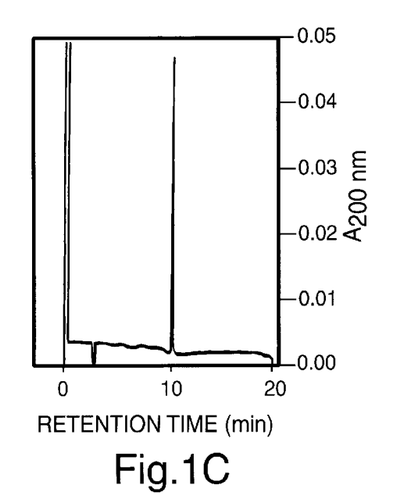

This resulted in a single peak of peptide (FIG. 1C).

Example 3

Characterisation of the Properties of Piscicolin 126.

Figure 2:
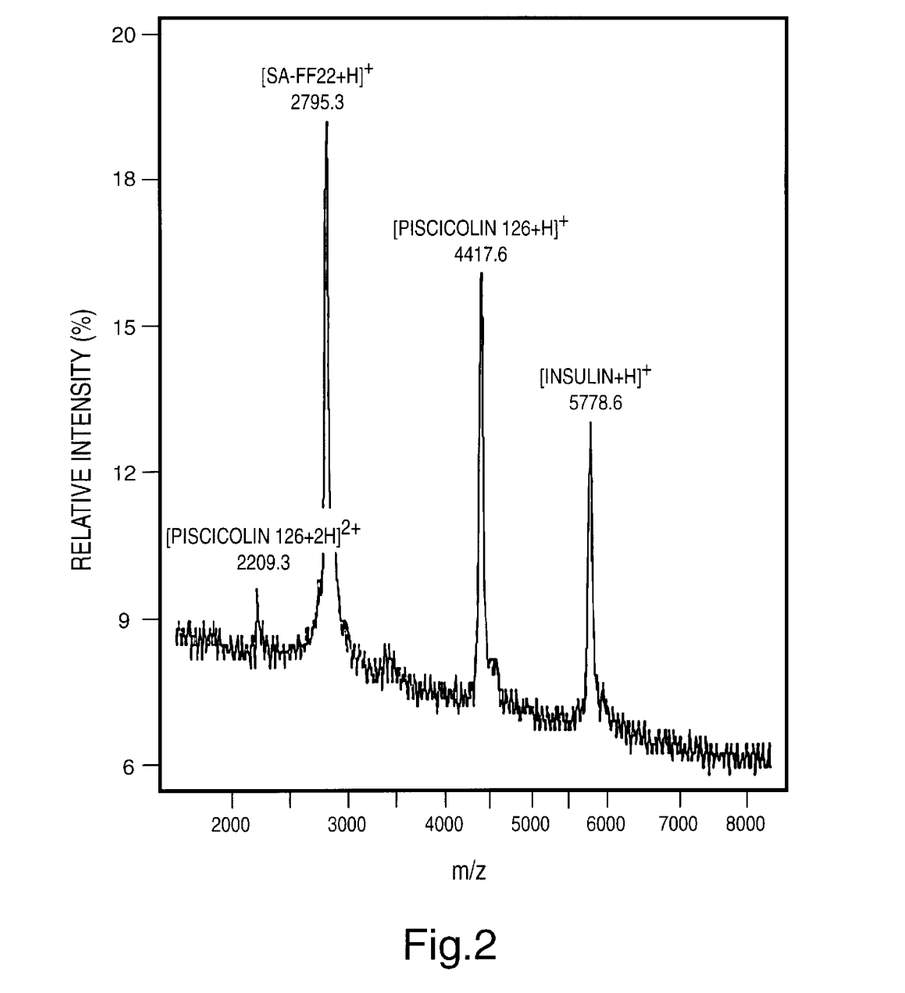
FIG. 2. MALDI-TOF mass spectrum of purified piscicolin 126.

The molecular weight ($M_r$) of piscicolin 126 was determined by MALDI-TOF mass spectrum analysis (FIG. 2). The peak of the piscicolin 126 corresponds to an $M_r$ of 4416.6±1.9 Da.

Piscicolin 126 was digested with a variety of enzymes, including some with proteolytic activity, and the digests were assessed for antimicrobial activity. The results are presented in Table 1 and indicate that the piscicolin 126 contains peptide material.

Table 1. Enzyme Inactivation of Piscicolin 126

20 µl enzyme solution (200 µg/ml in 0.2 M phosphate buffer, pH 7.0) was added to 200 µl of filter sterilised bacteriocin preparation. and incubated at 37° C. for 2 h. Residual bacteriocin activity (Arbitrary Units ml$^{-1}$) was determined by bioassay with *Listeria monocytogenes* 4A.

| Enzyme Treatment | Activity | |
|---|---|---|
| | AU ml$^{-1}$ | %[1] |
| Control | 12800 | 100 |
| Catalase | 12800 | 100 |
| α-Chymotrypsin | 0 | 0 |
| β-Chymotrypsin | 0 | 0 |
| Lipase | 12800 | 100 |
| Lysozyme | 12800 | 100 |
| Pepsin | 12800 | 100 |
| Protease I | 0 | 0 |
| Protease XIV | 400 | 3 |
| Protease XXIII | 0 | 0 |
| Trypsin | 800 | 6 |

[1] % refers to residual bacteriocin activity (following treatment) as a % of original activity, i.e., unaffected = 100%. completely destroyed = 0%.

Example 4

Determination of the Structure of Piscicolin 126

The amino acid sequence of the piscicolin 126 was determined. The sequence is presented in FIG. 3.

Figure 4A:
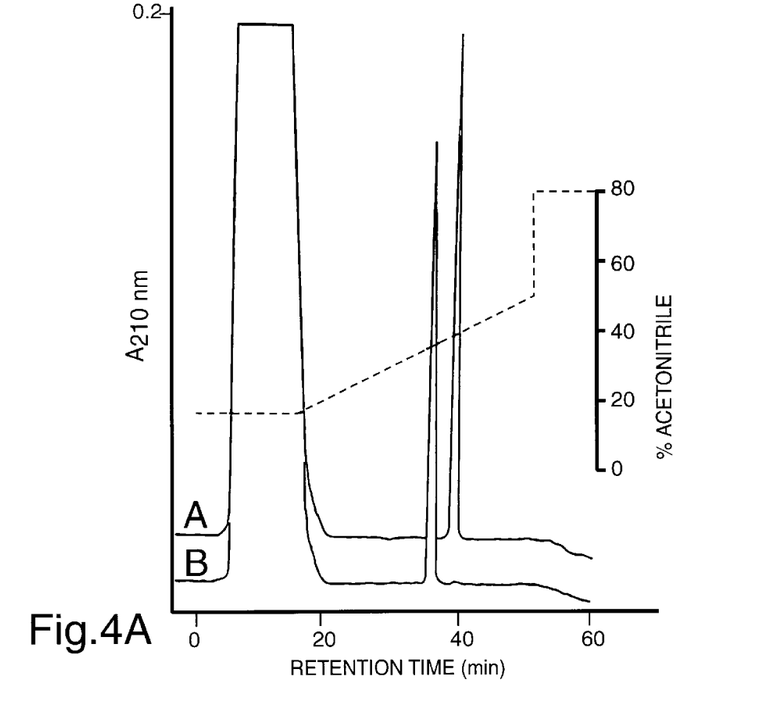
FIG. 4A: Reversed-phase HPLC separation of piscicolin 126 following treatment with 4-vinylpyridine in the (A) absence of and (B) presence of the reducing agent 2-mercaptoethanol. The collected peaks from each separation were analysed by MALDI-TOF mass spectrometry.
Figure 4B:
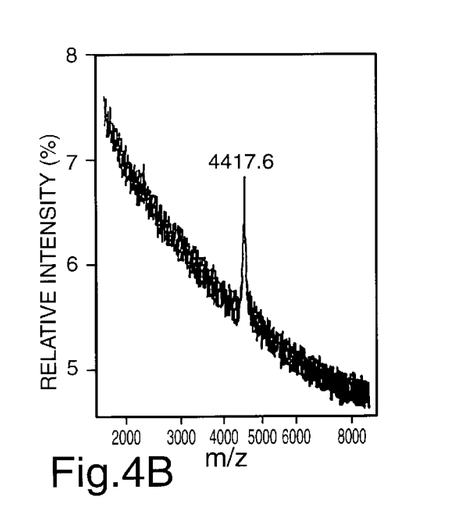
FIG. 4B: (C) peak material from A.
Figure 4C:
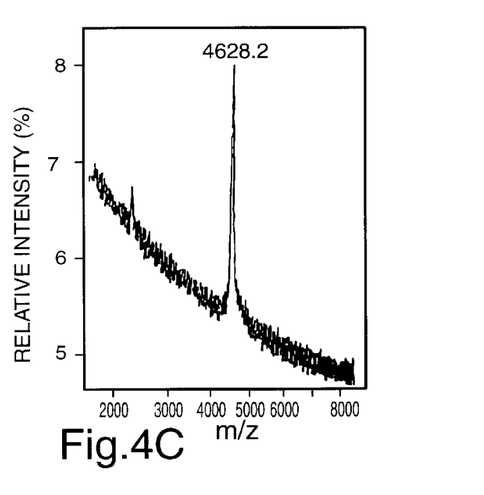

The presence or absence of free sulphydryl groups in piscicolin 126 was determined by analysis of the products formed following treatment of piscicolin 126 with the alkylating agent 4-vinylpyridine in either the presence or absence of the reducing agent 2-mercaptoethanol (FIG. 4). No mass increase was observed for the sample that had been reacted with 4-vinylpyridine in the absence of reducing agent FIG. 4C), indicating that piscicolin 126 does not contain free sulphydryl groups. The mass increase of 210 Da observed for the sample reacted with 4-vinylpyrridine in the presence of the reducing agent (FIG. 4D) corresponds to bipyridethylation and indicates that piscicolin 126 contains a disulphide bridge between two cysteine residues.

Example 5

Isolation and characterisation of the Gene Encoding Piscicolin 126

High molecular weight total DNA was isolated from bacterial strain JG126 and partially digested with restriction endonuclease Sau3AI. The cohesive ends were partially filled using Klenow DNA polymerase, dGTP and dATP and ligated into the partially filled Xho I sites of the arms of the LambdaGEM®-12 vector. The ligated DNA was packaged into phages and used to transfect *E.coli* strain LE392.

A piscicolin 126 specific gene probe was prepared by PCR amplification using the degenerate oligo-nucleotide primers 5'TG(CT)AA(CT)AA(AG)AA(CT)GG(ACGT)TG(CT) and 5'GC(CT)TT(AG)TTCCA(ACGT)CC(ACGT)GC(ACGT)GC(ACGT)CC and *C. piscicola* JG126 genomic DNA as template. The 107 bp PCR product was cloned into the pGEM®-T vector in the *E.coli* host PMC112 and the nucleotide sequence of the cloned fragment determined. Translation of the sequence confirmed that part of the piscicolin 126 gene had been cloned.

Figure 5:
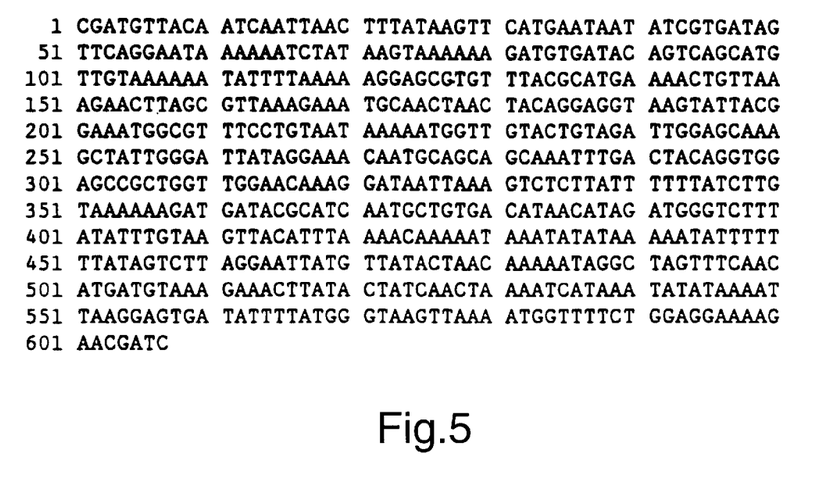
FIG. 5. DNA sequence of the 607 bp Hinf I/Sau 3A DNA fragment encoding the structural gene for Piscicolin 126.

The 107 bp PCR fragment was used to screen the genomic lambda library and a positive clone containing an insert of approximately 20 kb was isolated. From the lambda clone a 607 bp Hinf I/Sau 3A fragment was subcloned into pGEf®-7 in the *E.coli* host PMC112 and the nucleotide sequence of both strands determined (FIG. 5). Translation of the DNA sequence confirmed that the gene encoding the piscicolin 126 and its putative signal peptide had been cloned (FIG. 6).

Example 6

Spectrum of Antimicrobial Activity of Piscicolin 126

The spectrum of the antimicrobial -activity of piscicolin 126 has been tested against a number of pathogenic and non pathogenic bacteria and yeast strains.

The spectrum was determined in at least two separate tests against Gram-positive and Gram-negative bacteria and yeasts. Where a variable result occurred in the first two tests, the indicator reaction was tested a third time and the result used to determine an overall positive or negative reaction. The results are presented in Table 2.

Table 2. Antimicrobial Activity of Piscicolin 126.

Aliquots (5 µl) of a preparation of piscicolin 126 concentrated by ammonium sulphate precipitation were applied to the surface of agar plates and allowed to dry prior to overlaying with indicator cultures. After incubation, the inhibition of the indicator strain by piscicolin 126 was scored by the presence (+) or absence (−) of a zone of growth inhibition in the culture lawn.

| AFRICC Accession No | Indicator | Activity |
| --- | --- | --- |
| 0110 | *Aeromonas hydrophila* | − |
| 0303 | *Bacillus cereus* | − |
| 0312 | *Bacillus polvmyxa* | − |
| 0315 | *Bacillus stearothermophilus* | − |
| 0316 | *Bacillus stearothermophilus* var. *calidolactis* | − |
| 0320 | *Bacillus subtilis* | − |
| 0602 | *Brocothrix thermosphactum* | − |
| 0603 | *Brocothrix thermosphactum* | − |
| 0604 | *Brocothrix thermosphactum* | − |
| 0605 | *Brocothrix thermosphactum* | + |
| 0901 | *Clostridium botulinum* type B | − |
| 0914 | *Clostridium sporogenes* | − |
| 1001 | *Corynebacterium* sp. | − |
| 1105 | *Debaryomyces hansei* | − |
| 1201 | *Enterobacter aerogenes* NCTC 10006 | − |
| 1301 | *Escherichia coli* NCTC 8196 | − |
| 2001 | *Lactococcus diacetylactis* | − |
| 2002 | *Lactococcus cremoris* | − |
| 2010 | *Lactococcus lactis* | − |
| 2011 | *Lactococcus lactis* | − |
| 2101 | *Lactobacillus sake* | + |
| 2102 | *Lactobacillus plantarum* | − |
| 2103 | *Lactobacillus curvatus* | + |
| 2104 | *Lactobacillus* sp. | − |
| 2201 | *Leuconostoc mesentroides* var. *cremoris* | + |
| 2206 | *Leuconostoc cremoris* | − |
| 2208 | *Leuconostdc dextranicus* | + |
| 2301 | *Listeria denitrificans* ATCC 14570 | − |
| 2303 | *Listeria grayi* | + |
| 2305 | *Listeria innocua* | + |
| 2306 | *Listeria ivanovii* | + |
| 2310 | *Listeria monocvtogenes* 4A | + |
| 2311 | *Listeria monocytogenes* 4B | + |
| 2312 | *Listeria monocytogenes* | + |
| 2320 | *Listeria seeligeri* | + |
| 2321 | *Listeria seeligeri* | + |
| 2405 | *Micrococcus luteus* | − |
| 2406 | *Micrococcus luteus* | − |
| 2415 | *Micrococcus varians* | − |
| 2702 | *Pediococcus acidilactici* | − |
| 2703 | *Pediococcus acidilactici* | + |
| 2704 | *Pediococcus pentosaceus* | + |
| 3020 | *Proteus vulgaris* | − |
| 3101 | *Pseudomonas aeruginosa* | − |
| 3105 | *Pseudomonas fluorescens* | − |
| 3301 | *Saccharomvces cerevisiae* | − |
| 3410 | *Salmonella salford* | − |
| 3412 | *Salmonella typhimurium* | − |
| 3501 | *Serratia marcescens* | − |
| 3601 | *Staphylococcus aureus* NCTC 6571 | − |
| 3602 | *Staphylococcus aureus* | − |
| 3603 | *Staphylococcus aureus* | − |
| 3605 | *Staphylococcus camosus* | − |
| 3609 | *Staphylococcus epidermidis* NGTC 6513 | − |
| 3715 | *Streptococcus thermophilus* | + |
| 3716 | *Streptococcus thermophilus* | + |
| 3801 | *Yersinia enterocolitica* | − |
| 3901 | *Enterococcus faecalis* | + |
| 3902 | *Enterococcus faeceum* | + |
| 4001 | *Carnobacterium* sp. | + |

The results indicate that the bacteriocin has a limited spectrum of activity, and appears to act against food-borne pathogens and spoilage microorganisms but should have limited effect against beneficial bacteria such as cheese starter culture strains used in food systems.

Example 7

Quantitation of antimicrobial activity of piscicolin 126 against cheese starter bacteria.

The sensitivity of cheese starter bacteria to piscicolin 126 was tested in both artificial growth media and whole milk (Tables 3, 4 and 5).

Table 3. Minimum Inhibitory Concentration of piscicolin 126 tested against cheese starter bacteria.

A preparation of piscicolin 126 concentrated by ammonium sulphate precipitation was serially diluted in sterile distilled water and applied (5 µl) to the surface of MRS agar plates and allowed to dry prior to overlaying with indicator cultures. The amount of bacteriocin JG 126 activity in the concentrated preparation was determined as 204,800 AU $ml^{-1}$ by bioassay with *Listeria monocytogenes* 4A. After incubation. the minimum inhibitory concentration of piscicolin 126 against each strain of cheese starter bacteria was expressed as the lowest amount of activity of piscicolin 126 which demonstrated a distinct zone of growth inhibition in the culture lawn.

| Starter Culture Accession No. | Indicator | MIC (AU $ml^{-1}$) |
| --- | --- | --- |
| Mauri Laboratories Culture Collection (MLCC) | | |
| M124 | *Lactococcus lactis* subsp. *cremoris* | >204,800 |
| M126 | *Lactococcus lactis* subsp. *cremoris* | 51,200 |
| M145 | *Lactococcus lactis* subsp. *cremoris* | >204,800 |
| M149 | *Lactococcus lactis* subsp. *cremoris* | >204,800 |
| M193 | *Lactococcus lactis* subsp. *cremoris* | >204,800 |
| M379 | *Lactococcus lactis* subsp. *cremoris* | >204,800 |
| M229 | *Lactococcus lactis* subsp. *lactis* | >204,800 |
| M238 | *Lactococcus lactis* subsp. *lactis* | >204,800 |
| M262 | *Lactocoçpus lactis* subsp. *lactis* | >204,800 |
| M276 | *Lactococcus lactis* subsp. *lactis* | >204,800 |
| M392 | *Lactococcus lactis* subsp. *lactis* | >204,800 |
| M474 | *Lactococcus lactis* subsp. *lactis* | >204,800 |
| DRC | *Lactococcus lactis* subsp. *lactis* var *diacetyladis* | >204,800 |
| FDLD3 | *Lactococcus lactis* subsp. *lactis* var *diacetylactis* | >204,800 |
| HBD1 | *Lactococcus lactis* subsp. *lactis* var *diacetylactis* | >204,800 |
| HDD1 | *Lactococcus lactis* subsp. *lactis* var | >204,800 |

-continued

| Starter Culture Accession No. | Indicator | MIC (AU ml$^{-1}$) |
|---|---|---|
| | diacetylactis | |
| FLIL1 | Leuconostoc sp. | >204,800 |
| HLD1 | Leuconostoc sp. | >204,800 |
| ST3 | Streptococcus thermophilus | >204,800 |
| ST41 | Streptococcus thermophilus | >204,800 |
| ST42 | Streptococcus thermophilus | >204,800 |
| AFRI Culture Collection (AFRICC) | | |
| 2201 | Leuconostoc mesentroides var. cremoris | 102,400 |
| 2208 | Leuconostoc dextranicus | 102,400 |
| 3715 | Streptococcus thermophilus TS1 | 2,048 |
| 3716 | Streptococcus thermophilus TS2 | 3,200 |

The results indicate that, in plate bioassays with *Listeria monocytogenes* 4A, cheese starter bacteria are generally not sensitive to less than 2,048 AU ml$^{-1}$ of piscicolin 126 and most are not sensitive to 102,400 AU ml$^{-1}$ and higher concentrations.

Table 4. The effect of Piscicolin 126 on cheese starter culture activity in whole milk.

The effect of piscicolin 126 (2,048 AU ml$^{-1}$) on starter culture activity (rate of pH decrease) was determined in sterile whole milk at 30° C. (except for strains 3715 and 3716, where an incubation temperature of 37° C. was required to support more optimal growth). Cultures were grown in sterile skim milk (10% w/v) for 16 h at 30° C. or 37° C. (strains 3715 and 3716) and inoculated (10% v/v) into sterile whole milk to test starter activity in the absence and presence (2,048 AU ml$^{-1}$) of piscicolin 126. Uninoculated milk samples with and without added piscicolin 126 were used as controls. The pH of aliquots (2.5 ml) of samples removed under sterile conditions were determined at the times indicated.

| Starter culture Accession No. | JG126 | pH | | | | |
|---|---|---|---|---|---|---|
| | | 0 h | 2 h | 4 h | 6 h | 8.5 h |
| MLCC M276 | − | 5.92 | 5.70 | 5.14 | 4.53 | 4.27 |
| (Bacteriocin insensitive) | + | 5.87 | 5.66 | 5.12 | 4.50 | 4.28 |
| MLCC M126 | − | 6.00 | 5.72 | 5.15 | 4.54 | 4.25 |
| (Bacteriocin sensitive) | + | 6.04 | 5.76 | 5.27 | 4.64 | 4.30 |
| AFRICC 3715 | − | 5.89 | 5.75 | 5.47 | 5.22 | 5.04 |
| (Bacteriocin sensitive) | + | 5.87 | 5.76 | 5.44 | 5.18 | 5.01 |

The results indicate that piscicolin 126 at a level of 2,048 AU ml$^{-1}$ (as determined by plate bioassay with *Listeria monocytogenes* 4A) does not inhibit starter activity.

Table 5. The effect of piscicolin 126 on viable count of cheese starter cultures and *Listeria monocytogenes* 4A in whole milk.

The effect of piscicolin 126 (2,048 AU ml$^{-1}$) on viable count of the most bacteriocin-sensitive starter culture from each of the Mauri Laboratories (strain M126) and AFRI (strain 3715) culture collections (Table 3) and *Listeria monocytogenes* 4A (at initial levels of $10^4$ and $10^6$ cfu ml$^{-1}$) was determined in sterile whole milk (at 30° C. for strains M126 and 2310 and at 37° C. for strain 3715) at the times indicated. Viable counts were determined (as 0.1 ml spread plates of an appropriate dilution of the cultures) on M17 Agar (strains M126 and 3715) and Listeria Selective Agar (strain 2310).

| Culture | | JG126 | Viable count (log cfu ml$^{-1}$) | |
|---|---|---|---|---|
| | | | 0 h | 6 h |
| Starter cultures (on M17 Agar) | MLCC M126 | − | 6.71 | 8.51 |
| | | + | 6.63 | 8.52 |
| | AFRICC 3715 | − | 7.15 | 8.08 |
| | | + | 7.18 | 8.00 |
| *Listeria monocytogenes* 4A | inoculum $10^4$ cfu ml$^{-1}$ | − | 4.38 | 5.95 |
| | | + | <1.0 | <1.0 |
| AFRICC 2310 (on Listeria Selective Agar) | inoculum $10^6$ cfu ml$^{-1}$ | − | 6.24 | 7.72 |
| | | + | <1.0 | 2.94 |

The results indicate that the viable counts of cheese starter cultures were unaffected, whereas the viable count of *Listeria monocytogenes* was substantially reduced by the presence of piscicolin 126 in whole milk.

The piscicolin 126 therefore should find application as a preservative for foods and beverages.

Example 8

Antimicrobial Activity of Piscicolin 126 in Devilled Ham Paste and Ricotta Cheese Ricotta cheese (250 g) and Devilled Ham Paste (260 g) were inoculated with *Listeria monocytogenes* (AFRICC No. 2310) at $10^3$–$10^6$ cfu g$^{-1}$ in sterile stomacher bags. An aliquot (10 ml) of concentrated piscicolin 126 preparation was added and mixed thoroughly (Colworth stomacher, 60 s) to provide a final concentration of piscicolin 126 of approximately 2,048 AU g$^{-1}$ (as determined by plate bioassay). In control samples, sterile water was substituted for the piscicolin 126 preparation. Portions (10 g) of the mixtures were sealed in sterile stomacher bags and incubated at 10° C. for the length of the trial. At the times indicated. aliquots (90 ml) of peptone solution (0.1% w/v, pH 7) were added to portions of Ricotta cheese and mixed (Colworth stomacher, 60 s). Viable counts were determined on aliquots (0.1 ml) of appropriate dilutions of the mixed samples (in peptone solution) spread onto the surface of Listeria Selective Agar (Oxoid) plates. Viable count determinations were performed on each of three portions of Ricotta cheese and Devilled Ham Paste at the times indicated and are expressed as the mean value in Tables 6 and 7.

Table 6. Effect of Piscicolin 126 on Listeria monocytogenes 4A in Challenged Ricotta Cheese.

The effect of piscicolin 126 (2,048 AU g$^{-1}$) on the viable count of *Listeria monocytogenes* 4A (initial inoculum $10^4$ cfu g$^{-1}$) in Ricotta cheese spread was determined on Listeria Selective Agar (Oxoid) plates as the mean value of triplicate samples after incubation at 10° C., at the times indicated.

| | Viable count on Listeria Selective Agar (Log cfu $g^{-1}$) | | | | | |
|---|---|---|---|---|---|---|
| Treatment | Day 0 | Day 1 | Day 2 | Day 5 | Day 7 | Day 21 |
| Control | 4.49 | 4.85 | 5.57 | 7.20 | 7.67 | 8.26 |
| Piscicolin 126 | 2.12 | 2.00 | 2.52 | 4.08 | 4.95 | 7.87 |

Table 7. Effect of Piscicolin 126 on Listeria monocytogenes 4A in Challenged Devilled Ham Paste.

The effect of piscicolin 126 (2,048 AU $g^{-1}$) on the viable count of *Listeria monocytogenes* 4A (initial inoculum $10^3$ cfu $g^{-1}$) in devilled ham paste was determined on Listeria Selective Agar (Oxoid) plates as the mean value of triplicate samples after incubation at 10° C., at the times indicated.

| | Viable count on Listeria Selective Agar (Log cfu $g^{-1}$) | | | | | | |
|---|---|---|---|---|---|---|---|
| Treatment | Day 0 | Day 1 | Day 4 | Day 6 | Day 7 | Day 14 | Day 21 |
| Control | 3.26 | 3.16 | 5.10 | 6.05 | 6.87 | 9.49 | 9.76 |
| Piscicolin 126 | <2.0 | <2.0 | <2.0 | <2.0 | <2.0 | <2.0 | 5.83 |

The results indicate that under the experimental conditions growth of *Listeria monocytogenes* in Devilled Ham Paste is prevented by piscicolin 126 for between 14 and 21 days, while growth of *Listeria monocytogenes* in Ricotta cheese is inhibited for up to 7 days.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A substantially pure bacteriocin in which the bacteriocin has an amino acid sequence as shown in SEQ ID NO:5.

2. A method of preserving foods or beverages, the method comprising adding to the food or beverage an effective antimicrobial amount of a bacteriocin as claimed in claim 1.

3. A composition of matter comprising a cheese starter culture and a bacteriocin as claimed in claim 1.

* * * * *